United States Patent

Warpehoski et al.

[11] Patent Number: 5,804,593
[45] Date of Patent: Sep. 8, 1998

[54] α-AMINO SULFONYL HYDROXAMIC ACIDS AS MATRIX METALLOPROTEINASE INHIBITORS

[75] Inventors: Martha A. Warpehoski, Portage; Mark Allen Mitchell, Kalamazoo; Eric Jon Jacobsen, Portage, all of Mich.

[73] Assignee: Pharmacia & Upjohn Company, Kalamazoo, Mich.

[21] Appl. No.: 953,940

[22] Filed: Oct. 20, 1997

Related U.S. Application Data

[60] Provisional application No. 60/029,585, Oct. 22, 1996.
[51] Int. Cl.[6] .......................... A61K 31/40; A61K 31/19; C07D 209/12; C07D 209/18
[52] U.S. Cl. ........................ 514/419; 514/575; 548/494; 562/623
[58] Field of Search ........................... 548/494; 562/623; 514/419, 575

[56] References Cited

FOREIGN PATENT DOCUMENTS

| | | |
|---|---|---|
| 0606046 A1 | 12/1993 | European Pat. Off. . |
| 757037 A2 | 7/1996 | European Pat. Off. . |
| 757984 A1 | 8/1996 | European Pat. Off. . |
| 95/35275 | 6/1995 | WIPO . |
| 95/35276 | 6/1995 | WIPO . |
| 96/27583 A1 | 3/1996 | WIPO . |
| 96/33172 A1 | 4/1996 | WIPO . |
| 96/40101 A1 | 6/1996 | WIPO . |
| 97/18194 A1 | 11/1996 | WIPO . |
| 96/20824 | 12/1996 | WIPO . |
| 97 27174 A | 7/1997 | WIPO . |

OTHER PUBLICATIONS

MacPherson, L. J. at el. *J. Med. Chem.* vol. 40, pp. 2525–2523, (1997).

*Primary Examiner*—William R. A. Jarvis
*Attorney, Agent, or Firm*—Lucy X. Yang

[57] ABSTRACT

A compound of formula I or pharmaceutical acceptable salts thereof,

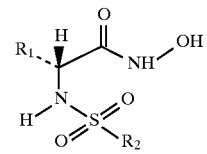

wherein $R_1$ is isopropyl, 2-methylbut-2yl, phenyl, benzyl, or 1H-indol-3ylmethyl; $R_2$ is n-octyl, phenyl, or phenyl substituted with methoxy, fluoro, or bromo, are matrix metalloproteinase inhibitors.

11 Claims, No Drawings

α-AMINO SULFONYL HYDROXAMIC ACIDS AS MATRIX METALLOPROTEINASE INHIBITORS

CROSS-REFERENCE TO RELATED APPLICATION

This application claims the benefit of the following provisional application: U.S. Ser. No. 60/029,585, filed Oct. 22, 1996, under 35 USC 119(e)(i).

FIELD OF THE INVENTION

The present invention relates to therapeutically active α-amino sulfonyl hydroxamic acids, to pharmaceutical compositions containing them, and to the method of using such compounds. Particularly, the compounds of the invention are inhibitors of matrix metalloproteinases involved in tissue degradation.

BACKGROUND OF THE INVENTION

Loss of connective tissue integrity occurs in many disease processes, including osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, and other diseases related to connective tissue degradation. Although there is a high incidence of these diseases in the developed world, there is no treatment that prevents the tissue damage that occurs. Considerable lines of scientific evidence indicate that uncontrolled connective matrix metalloproteinase (MMPs) activity is responsible for the damage, and as a consequence the inhibition of these enzymes has become the target for therapeutic intervention (see Matrisian, L. M., Bases, Vol. 14, pp 445–463, (1992); Emonard, H. et al., Cellular and molecular Biology, Vol. 36, pp 131–153, (1990); Docherty, A. J. P. et al., Annals of the Rheumatic, Vol. 49, pp 469–479, (1990)).

Hydroxamic acid derivatives are a class of known therapeutically active MMPs inhibitors and there are numerous references in the art disclosing a variety of hydroxamic acid derivatives. This invention provides α-amino sulfonyl hydroxamic acids wherein the hydrogen on the amino nitrogen is unsubstituted and wherein there is a side chain on the α-carbon position. The compounds of the present invention have unexpected superior activity in inhibiting various enzymes from the matrix metalloproteinase family, predominantly gelatinase, and hence are useful for the treatment of matrix metallo endoproteinase diseases such as osteoporosis, tumor metastasis (invasion and growth), periodontitis, gingivitis, corneal ulceration, dermal ulceration, gastric ulceration, inflammation, and other diseases related to connective tissue degradation.

INFORMATION DISCLOSURE

The following patent publications disclose sulfonamide hydroxamic acids as matrix metalloproteinase inhibitors:

European Patent Publication 0,606,046 A1 discloses arylsulfonamido-substituted hydroxamic acids useful as matrix metalloproteinase inhibitors.

International Publication No. WO 95/35275 and WO 95/35276 disclose hydroamic acid and carboxylic acid derivatives useful as matrix metalloproteinases inhibitors.

International Publication No. WO 96/40101 A1 discloses new use of arylsulfonamido-substituted hydroxamic acids in the treatment of carcinoma and tumor angiogenesis.

International Publication No. WO 96/27583 A1 discloses arylsulfonamido N-hydroxamic acid derivatives of butyric acid useful as metalloproteinases inhibitors.

International Publication No. WO 96/33172 A1 discloses arylsulfonyl hydroxamic acid derivatives as matrix metalloproteinases and TNF inhibitors.

International Publication No. WO 97/20824 discloses benzenesulfonyl hydroxamic acids as metalloproteinase inhibitors.

International Publication No. WO 97/18194 A1 discloses cyclic and heterocyclic N-substituted α-iminohydroxamic and carboxylic acids as metalloproteinase inhibitors.

European Patent Publication 757984 A1 discloses hydroxamic acid derivatives as gelatinase inhibitors useful treating rheumatoid diseases.

European Patent Publication 757037 A2 discloses arylsulfonamidoamino acid derivatives useful as matrix metalloproteinase inhibitors.

MacPherson, L. J. at el. *J. Med. Chem.* Vol. 40, pp 2525–2523, (1997) discloses structure-activity relationships of a lead hydrocamic acids as matrix metalloproteinase inhibitors.

SUMMARY OF THE INVENTION

The present invention provides a compound of formula I

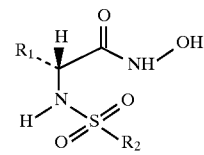

or pharmaceutical acceptable salts thereof wherein $R_1$ is isopropyl, 2-methylbut-2-yl, phenyl, benzyl, or 1H-indol-3-yl-methyl; and $R_2$ is n-octyl, phenyl, or phenyl substituted with methoxy, fluoro, or bromo.

The compounds of the present invention inhibit various enzymes from the matrix metalloproteinase family, predominantly gelatinase, and hence are useful as preventatives and therapeutics for diseases related to connective tissue degradation.

DETAILED DESCRIPTION OF THE INVENTION

For the purpose of the present invention, the term "pharmaceutically acceptable salts" refers to salts useful for administering the compounds of this invention and these include hydrochloride, hydrobromide, hydroiodide, trifluoroacetic acid, sulfate, phosphate, acetate, propionate, lactate, mesylate, maleate, malate, succinate, tartrate, citrate, 2-hydroxyethyl sulfonate, fumarate and the like. These salts may be in hydrated form. Some of the compounds of this invention may form metal salts such as sodium, potassium, calcium and magnesium salts and these are embraced by the term "pharmaceutically acceptable salts".

The compounds of the present invention can be converted to their salts according to conventional methods.

The $R_1$ substituent is isopropyl, 2-methylbut-2yl, phenyl, benzyl, or 1H-indol-3ylmethyl.

The $R_2$ substituent is n-octyl, phenyl, p-methoxyphenyl, p-fluorophenyl, or p-bromophenyl.

The compounds of formula I of this invention contain a chiral center at α-position of amino acids, as such there exist two enantiomers or a racemic mixture of both. This invention relates to the compounds having R-configuration under the Cahn-Ingold-Prelog nomenclature system.

The compounds of this invention include the followings:

a. N-Hydroxy-2(R)-[(4- methoxybenzenesulfonyl)amino]-3-(3-indolyl)-propanamide, b. N-Hydroxy-2(R)-[(benzenesulfonyl)amino]-3-(3-indolyl)-propanamide, c. N-Hydroxy-2(R)-[(4-fluorobenzenesulfonyl)amino]-3-(3-indolyl)-propanamide, d. N-Hydroxy-2(R)-[(4-methoxybenzenesulfonyl)amino]-3-phenyl-propanamide, e. N-Hydroxy-2(R)-[(4-bromobenzenesulfonyl)amino]-3-(3-indolyl)-propanamide, f. N-Hydroxy-2(R)-[(n-octylsulfonyl)amino]-3-(3-indolyl)-propanamide, g. N-Hydroxy-2(R)-[(4-methoxybenzenesulfonyl)amino]-2-phenyl acetamide, h. N-Hydroxy-2(R)-[(4-methoxybenzenesulfonyl)amino]-3-methyl butanamide, i. N-Hydroxy-2(R)-[(benzenesulfonyl)amino]-3-methyl butanamide, or j. N-Hydroxy-2(R)-[(4-methoxybenzenesulfonyl)amino]-3,3-dimethyl pentanamide.

The compounds of this invention can be prepared in accordance to the process discussed below.

In CHART I, $R_1$ and $R_2$ are the groups as defined previously; R' is either hydrogen or a low alkyl or an (un)substituted phenyl. Structure 1 are sulfonylated in the presence of an appropriate base such as tertiary amine or pyridine to afford sulfonamide 2 or 3 directly. The reaction may be carried out in a solvent which does not adversely affect the reaction (e.g. dichloromethane, diethylether, tetrahydrofuran or a mixture thereof). All of the starting amino acid acids or esters in the present invention are commercially available or can be prepared readily by one having ordinary skill in the art of organic chemistry, utilizing well known reactions. Saponification of compound 2 to carboxylate 3 occurs efficiently under either acidic or basic conditions. Direct coupling of carboxylate 3 with hydroxylamine provides the desired hydroxamates 5.

CHART I

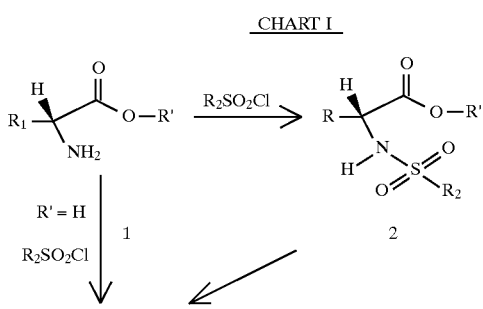

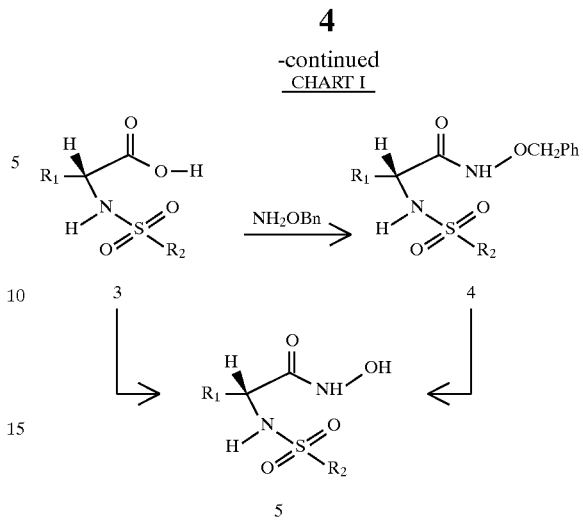

In this reaction, chromatography on silica gel is generally employed to purify the hydroxamates. Alternatively, carboxylate 3 is reacted with O-benzylhydroxylamine. This reaction provides a coupled product 4 which is more soluble in organic solvents, therefore, to allow easy isolation. Hydrogenolysis of the benzyl group by the methods well known to those skilled in the art afford compound 5. The pharmaceutical compositions of this invention may be prepared by combining the compounds of formula I of this invention with a solid or liquid pharmaceutically acceptable carrier, and optionally, with pharmaceutically acceptable adjuvants and excipients employing standard and conventional techniques. Solid form compositions include powders, tablets, dispersible granules, capsules and suppositories. A solid carrier can be at least one substance which may also function as a diluent, flavoring agent, solubilizer, lubricant, suspending agent, binder, tablet disintegrating agent, and encapsulating agent. Inert solid carriers include magnesium carbonate, magnesium stearate, talc, sugar, lactose, pectin, dextrin, starch, gelatin, cellulosic materials, low melting wax, cocoa butter, and the like. Liquid form compositions include solutions, suspensions and emulsions. For example, there may be provided solutions of the compounds of this invention dissolved in water, water-propylene glycol, and water-polyethylene glycol systems, optionally containing conventional coloring agents, flavoring agents, stabilizers and thickening agents.

The pharmaceutical composition is provided by employing conventional techniques. Preferably the composition is in unit dosage form containing an effective amount of the active component, that is, the compounds of formula I according to this invention.

The quantity of active component, that is the compounds of formula I according to this invention, in the pharmaceutical composition and unit dosage form thereof may be varied or adjusted widely depending upon the particular application method, the potency of the particular compound and the desired concentration. Generally, the quantity of active component will range between 0.5% to 90% by weight of the composition.

In therapeutic use for treating a patient, suffering from or susceptible to diseases involving connective tissue degradation, or inhibiting various enzymes from the matrix metalloproteinase family, including collagenase, stromelysin, and gelatinase, the compounds or pharmaceutical compositions thereof will be administered orally, parenterally and/or topically at a dosage to obtain and maintain a concentration, that is, an amount, or blood-level of active component in the patient undergoing treatment which will be effective to inhibit such enzymes. Generally, an effective amount of the active compound will be in the range of about 0.1 to about 100 mg/kg. It is to be understood that the dosages may vary depending upon the requirements of the patient, the severity of connective tissue degradation being treated, and the particular compounds being used. Also, it is to be understood that the initial dosage administered may be increased beyond the above upper level in order to rapidly achieve the desired blood-level or the initial dosage may be smaller than the optimum and the daily dosage may be progressively increased during the course of treatment depending on the particular situation. If desired, the daily dose may also be divided into multiple doses for administration, e.g., two to four times per day.

The compounds of the present invention inhibit various enzymes from the matrix metalloproteinase family, predominantly gelatinase, and hence are useful for the treatment of matrix metallo endoproteinase diseases such as osteoarthritis, rheumatoid arthritis, septic arthritis, osteopenias such as osteoporosis, tumor metastasis (invasion and growth), periodontitis, gingivitis, corneal ulceration, dermal ulceration, gastric ulceration, various enzymes from the matrix metalloproteinase family, predominantly collagenase and other diseases related to connective tissue degradation. Such diseases and conditions are well known and readily diagnosed by physician of ordinary skill.

Pharmaceutical compositions for parenteral administration will generally contain a pharmaceutically acceptable amount of the compounds according to formula I as a soluble salt (acid addition salt or base salt) dissolved in a pharmaceutically acceptable liquid carrier such as, for example, water-for-injection and a suitably buffered isotonic solution having a pH of about 3.5–6. Suitable buffering agents include, for example, trisodium orthophosphate, sodium bicarbonate, sodium citrate, N-methylglucamine, L(+)-lysine and L(+)-arginine, to name a few. The compounds according to formula I generally will be dissolved in the carrier in an amount sufficient to provide a pharmaceutically acceptable injectable concentration in the range of about 1 mg/ml to about 400 mg/ml. The resulting liquid pharmaceutical composition will be administered so as to obtain the above-mentioned inhibitory effective amount of dosage. The compounds of formula I according to this invention are advantageously administered orally in solid and liquid dosage forms.

The compounds and their preparations of the present invention will be better understood in connection with the following examples, which are intended as an illustration of and not a limitation upon the scope of the invention.

EXAMPLE 1

Preparation of N-hydroxy-2(R)-[(4-methoxybenzenesulfonyl)-amino]-3-(3-indolyl)-propanamide

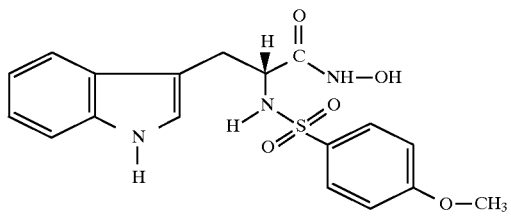

Step 1

Preparation of 2(R)-[(4-methoxybenzenesulfonyl) amino]-3-(3-indolyl)-propanoic acid methyl ester To a suspension of D-tryptophan methyl ester hydrochloride (4 mmol) in 40 mL of methylene chloride, magnetically stirred and cooled in an ice bath, under a nitrogen atmosphere, is added 8 mmol of NMM and 4 mmol of 4-methoxybenzene sulfonyl chloride. The mixture is allowed to come to ambient temperature overnight. It is diluted with ethyl acetate and washed twice with aqueous 10% HCl, then successively with water, 1M sodium bicarbonate, and brine. The organic solution is dried over sodium sulfate and concentrated to afford 1.05 g (65%) of a white solid, m.p. 120°–122° C.

Step 2

Preparation of 2(R)-[(4-methoxybenzenesulfonyl) amino]-3-(3-indolyl)-propanoic acid To 1.3 mmol of 2(R)-[(4-methoxybenzenesulfonyl) amino]-3-(3-indolyl)-propanoic acid methyl ester suspended in 15 mL of ethanol is added 5 mL of aqueous 2.5M sodium hydroxide. The solid suspension dissolved, and is allowed to stir at ambient temperature overnight. The mixture is acidified with aqueous 10% HCl and extracted with ethyl acetate. The organic phase is washed with brine and dried over sodium sulfate. It is concentrated to afford 0.45 g (93%) of a white solid, Step 3

Preparation of N-hydroxy-2(R)-[(4-methoxybenzenesulfonyl)amino]-3-(3-indolyl)-propanamide To 2(R)-[(4-methoxybenzenesulfonyl)amino]-3-(3-indolyl)-propanoic acid (0.67 mmol) in 6 mL of methylene chloride and 1 mL of DMF, cooled in an ice-bath, under a nitrogen atmosphere, is added 0.83 mmol of HOBT, 0.72 mmol of EDC, and 0.73 mmol of NMM. The mixture is allowed to stir for one hour. In a small test tube, 1 mmol of hydroxylamine hydrochloride and 0.9 mmol of NMM in 1 mL of DMF is agitated, forming a fine suspension which is then introduced into the carbodiimide reaction mixture. The mixture is allowed to come to ambient temperature overnight. It is diluted with 50 mL each of aqueous 10% HCl and ethyl acetate. The organic phase is washed with 10% HCl, twice with 1M sodium bicarbonate, and brine. It is dried over sodium sulfate, concentrated, and chromatographed on silica gel, eluting with 30% acetone and 1% acetic acid in methylene chloride. Fractions containing the hydroxamic acid product are pooled and concentrated to afford 135 mg (52%) of a white solid, $^1$H NMR (DMSO-$d_6$) δ10.75, 10.6, 8.79, 7.91, 7.46, 7.24, 6.99, 6.97, 6.87, 6.82, 3.76, 3.72, 2.91, 2.64. MS (FAB) m/z 779, 390, 389, 329, 130. IR (mull) cm$^{-1}$ 3324, 2925, 1665, 1595, 1497, 1458, 1261, 1157. [α]$_D$=+66° (0.62, ethanol).

EXAMPLE 2

Preparation of N-hydroxy-2(R)-[(benzenesulfonyl)amino]-3-(3-indolyl)-propanamide

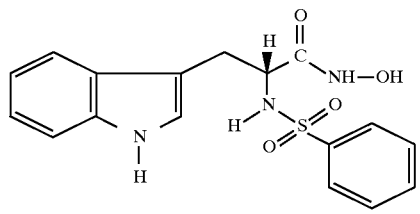

Following the general procedure outlined in EXAMPLE 1 (steps 1–3), and making non-critical variations but starting with benzenesulfonyl chloride, the title compound is obtained as a white solid. $^1$H NMR (DMSO-d$_6$) δ0.8, 10.6, 8.79, 8.13, 7.59–7.22, 7.03–6.86, 3.79, 2.93, 2.64 MS (EI) m/z: 359, 202, 157, 130. [α]$_D$=+38° (1.75, ethanol).

EXAMPLE 3

Preparation of N-hydroxy-2(R)-[(4-fluorobenzenesulfonyl)-amino]-3-(3-indolyl)-propanamide

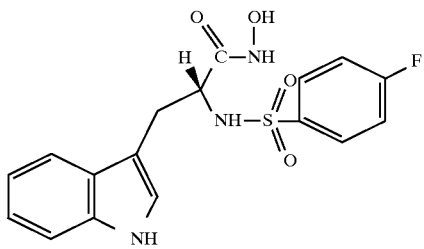

Following the general procedure outlined in EXAMPLE 1 (steps 1–3), and making non-critical variations but starting with 4-fluorobenzenesulfonyl chloride, the title compound is obtained. $^1$H NMR (d$_6$-DMSO) δ10.8, 10.7, 8.90, 8.25, 7.56–7.6, 7.38, 7.31, 7.00–7.14, 6.96, 3.86, 2.76–2.10. MS (FAB) m/z: 378, 378, 147, 130, 73, 69, 58, 57, 55, 43, 41.

EXAMPLE 4

Preparation of N-hydroxy-2(R)-[(4-methoxybenzenesulfonyl)-amino]-3-phenyl-propanamide

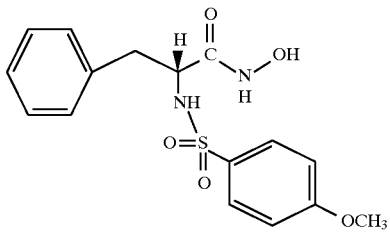

Following the general procedure outlined in EXAMPLE 1 (steps 1–3), and making non-critical variations but starting with D-phenylalanine methyl ester hydrochloride, the title compound is obtained. $^1$H NMR (d$_6$-DMSO) δ10.7, 8.88, 8.05, 7.56, 7.21–7.23, 7.09–7.11, 6.98, 3.86, 3.79–3.82, 2.56–2.85. MS (FAB) m/z: 351, 290, 236, 123, 75, 57.

EXAMPLE 5

Preparation of N-hydroxy-2(R)-[(4-bromobenzenesulfonyl)-amino]-3-(3-indolyl)-propanamide

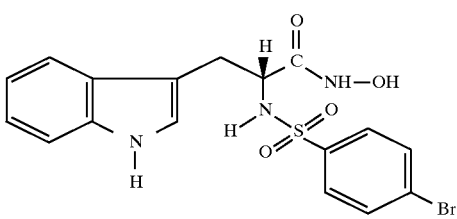

Step 1

Preparation of 2(R)-[(4-bromobenzenesulfonyl)amino]-3-(3-indolyl)-propanoic acid methyl ester To 1 g (3.9 mmol) of D-tryptophan methyl ester hydrochloride in 12 mL of pyridine at ambient temperature is added 1 g (3.9 mmol) of 4-bromobenzene sulfonyl chloride. The yellow mixture is allowed to stir overnight. It is then poured into aqueous 10% HCl and extracted with several portions of ethyl acetate. The combined organic phases are washed with aqueous 10% HCl, water, and brine, and dried over sodium sulfate. The solution is decolorized with activated charcoal, and concentrated to 1.1 g (65%) of a white solid.

Step 2

Preparation of N-hydroxy-2(R)-[(4-bromobenzenesulfonyl)amino]-3-(3-indolyl)-propanamide Following the general procedure outlined in EXAMPLE 1 (steps 2 and 3), and making non-critical variations but starting with 2(R)-[(4-bromobenzenesulfonyl)-amino]-3-(3-indolyl)-propanoic acid methyl ester, the title compound is obtained as an off-white solid. $^1$H NMR (DMSO-d$_6$) δ10.7, 8.86, 8.29, 7.41, 7.34, 7.28, 7.24, 7.03–6.98, 6.88, 3.78, 2.90, 2.70. IR (mull) cm$^{-1}$ 2924, 1665, 1458, 1161, 741. MS (FAB) m/z 440, 439, 438, 437, 379, 377, 130. [α]$_D$=+61° (0.7, methanol).

EXAMPLE 6

Preparation of N-hydroxy-2(R)-[(n-octylsulfonyl)amino]-3-(3-indolyl)-propanamide

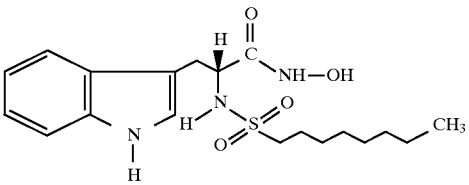

Following the general procedure outlined in EXAMPLE 7 (step 1) and making non-critical variations but starting with n-octylsulfonyl chloride, 2(R)-[(n-octylsulfonyl)amino]-3-(3-indolyl)-propanoic acid methyl ester is obtained as a colorless oil. $^1$H NMR (CDCl$_3$) δ8.28, 7.57, 7.35, 7.19, 7.12, 7.05, 5.0, 4.44, 3.72, 3.32, 3.24, 2.73, 1.65–1.50, 1.29–1.15, 0.88.

Following the general procedure outlined in EXAMPLE 1 (steps 2–3) and making non-critical variations but starting with 2(R)-[(n-octylsulfonyl)amino]-3-(3-indolyl)-propanoic acid methyl ester, the title compound is obtained as a glassy solid. $^1$H NMR (DMSO-d$_6$) δ10.9, 10.8, 9.0, 7.62, 7.54, 7.31, 7.17, 7.07, 7.0, 3.9, 3.05–2.9, 2.4, 1.3–0.9, 0.86. MS (EI) m/z: 395, 334, 174), 157, 130. [α]$_D$=+30° (0.8, ethanol).

EXAMPLE 7

Preparation of N-hydroxy-2-[(4-methoxybenzenesulfonyl)amino]-2-phenyl acetamide

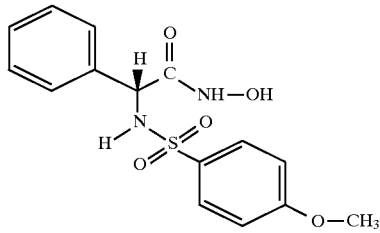

Step 1

Preparation of 2(R)-[(4-methoxybenzenesulfonyl)amino]-2-phenyl acetic acid methyl ester.

To 6 mmol of (R)-phenyl glycine methyl ester (hydrochloride salt [α]$_D$=–111° (1.34, aqueous 10% HCl)) in 10 mL of pyridine at ambient temperature is added 6.7 mmol of 4-methoxybenzene sulfonyl chloride. The yellow mixture is allowed to stir overnight. It is then poured into aqueous 10% HCl and extracted with several portions of ethyl acetate. The combined organic phases are washed with aqueous 10% HCl, water, and brine, and dried over sodium sulfate. The solution is concentrated to 2 g (quantitative yield) of a solid.

Step 2

Preparation of 2(R)-[(4-methoxybenzenesulfonyl)amino]-2-phenyl acetic acid

To a suspension of 3 mmol of 2(R)-[(4-methoxybenzenesulfonyl)amino]-2-phenyl acetic acid methyl ester in 15 mL of ethanol is added 5 mL of aqueous 2.5M sodium hydroxide. The solid suspension dissolved, and is allowed to stir, stoppered, at ambient temperature overnight. The resulting suspension is acidified with aqueous 10% HCl and extracted with ethyl acetate, adding brine to facilitate phase separation. The organic phase is washed with water and with brine and dried over sodium sulfate. It is concentrated to afford 0.95 g (quantitative yield) of a white solid.

Step 3

Preparation of N-hydroxy-2(R)-[(4-methoxybenzenesulfonyl)amino]-2-phenyl acetamide Following the general procedure outlined in EXAMPLE 1 (step 3), and making non-critical variations but starting with 2(R)-[(4-methoxybenzenesulfonyl)-amino]-2-phenyl acetic acid, the title compound is obtained as a white solid. $^1$H NMR (DMSO-d$_6$) δ10.85, 8.91, 8.44, 7.57, 7.23–7.16, 6.90, 4.78, 3.76. IR (mull) cm$^{-1}$ 3261, 2924, 1639, 1596, 1453, 1333, 1263, 1157. MS (FAB) m/z: 337, 276, 150. [α]$_D$=–4.4° (0.87, ethanol). Calc'd for C$_{15}$H$_{16}$N$_2$O$_5$S: C, 53.6; H, 4.79; N, 8.33. Found: C, 53.55; H, 4.84; N, 8.25.

EXAMPLE 8

Preparation of N-hydroxy-2(R)-[(4-methoxybenzenesulfonyl)-amino]-3-methyl butanamide

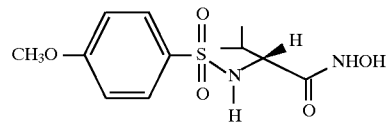

Step 1

Preparation of N-benzyloxy-2(R)-[(4-methoxybenzenesulfonyl)amino]-3-methyl butanamide To a solution of N-(p-methoxybenzenesulfonyl)-D-valine (1.01 g, 3.53 mmol) in CH$_2$Cl$_2$ (25 mL) are added the following reagents in the order given: HOBT (477 mg, 3.53 mmol), 4-methylmorpholine (1.95 mL, 17.7 mmol), O-benzylhydroxylamine hydrochloride (1.69 mg, 10.6 mmol), and EDC (880 mg, 4.59 mmol). The resultant slurry is stirred overnight (20 h) at room temperature. The solvent is evaporated and the residual material purified by silica gel chromatography (50 g of SG, EtOAc) to give 1.89 g of an impure solid; the solid is reconstituted in EtOAc (150 mL) and washed with 1 N HCl (3×50 mL) and brine (50 mL). The organic layer is dried over anhydrous Na$_2$SO$_4$, filtered, and concentrated to yield 1.11 g (79%) of product. The material is recrystallized from hot EtOAc/hexane to yield 779 mg of the title compound, as a white solid. mp 156°–158° C.; [α]$^{25}$$_D$+11° (c 1.01, CHCl$_3$); IR (mineral oil) 3252, 1657, 1596, 1502, 1445, 1354, 1328, 1306, 1266, 1165, 1160, 1146, 1096, 748, 671 cm$^{-1}$;$^1$H NMR (300 MHz, CDCl$_3$) δ8.56, 7.77, 7.36, 6.96, 5.22, 4.65–4.80, 3.84, 3.30–3.40, 1.90–2.05 , 0.70–0.90.

Step 2

Preparation of N-hydroxy-2(R)-[(4-methoxybenzenesulfonyl)amino]-3-methyl butanamide A solution of N-benzyloxy-2(R)-[(4-methoxybenzenesulfonyl)amino]-3-methyl butanamide, the product of step 1, in 50% MeOH/EtOAc (30 mL) is degassed with N$_2$ and treated with Pearlman's catalyst (160 mg). The atmosphere is replaced with H$_2$ via a balloon. After 3 hours, the reaction mixture is filtered through celite, washing the residual cake with excess MeOH and EtOAc. The filtrate is concentrated to give 620 mg of a white solid. The material is crystallized from hot MeOH/CH$_2$Cl$_2$ and hexane to give the title compound (345 mg, 56%) as a white, crystalline solid (mp 166°–168° C.). The mother liquor also yielded 251 mg (for a total yield of 97%) of additional product. [α]$^{25}$$_D$–4° (c 0.93, DMSO); IR (mineral oil) 3269, 1634, 1599, 1539, 1497, 1337, 1310, 1261, 1162, 1096, 1025, 845, 804, 674, 629 cm$^{-1}$; $^1$H NMR (300 MHz, DMSO-d$_6$) δ10.51, 8.81, 7.65–7.85, 7.69, 7.05, 3.83, 3.20–3.30, 1.65–1.80, 0.60–0.90; MS (EI) m/z 302 (M$^+$), 259, 242, 171, 107, 92, 76; Anal: C, 47.76; H, 6.30; N, 9.33; S, 10.27.

EXAMPLE 9

Preparation of N-hydroxy-2(R)-[(benzenesulfonyl)amino]-3-methyl butanamide

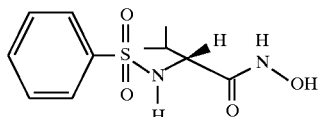

Step 1

Preparation of (R)-[2-methyl-1-[[(phenylmethoxy)amino]-carbonyl]propyl]-carbamic acid, 1,1-dimethylethyl ester CDI (2.45 g, 15.1 mmol) is added to a solution of N-(tert-butoxycarbonyl)-D-valine (3.28 g, 15.1 mmol) and CH$_2$Cl$_2$ (60 mL). The solution is stirred for 1 hour at room temperature. Diisopropylethylamine (2.90 mL, 16.6 mmol) and O-benzylhydroxylamine (2.64 g, 16.5 mmol) are added and the solution stirred for 16 hours at room temperature. The solution is concentrated, diluted with EtOAc, and washed with 5% HCl (2×50 mL), NaHCO$_3$ (50 mL) and brine (50 mL). The organic solution is dried (MgSO$_4$), filtered, and concentrated to give 4.42 g (91%) of the title compound as a white solid which is carried on crude.

Step 2

Preparation of D-2-amino-N-(benzyloxy-3-methyl-butylamide

TFA (8.0 mL) is added to a solution of (R)-[2-methyl-1-[[(phenylmethoxy)-amino]carbonyl]propyl]-carbamic acid, 1,1-dimethylethyl ester, the product of step 1, (1.00 g, 3.10 mmol) and CH$_2$Cl$_2$ (10.0 mL) at 0° C. The solution is stirred at 0° C. for 1 hour and is concentrated. Basic workup (CH$_2$Cl$_2$, NaHCO$_3$, MgSO$_4$) gives 665 mg (96%) of the title compound as a white solid which is carried on crude.

Step 3

Preparation of N-benzyloxy-2(R)-[(benzenesulfonyl)amino]-3-methyl butanamide

Benzenesulfonyl chloride (280 µL, 2.19 mmol) is added to a cold (0° C.) solution of D-2-amino-N-(benzyloxy)-3-methyl-butyramide, the product of step 2, (442 mg, 1.99 mmol) and Hunig's base (380 µL, 2.18 mmol) in CH$_2$Cl$_2$ (20 mL). After 1 hour at 0° C., the solution is allowed to warm to room temperature overnight. The reaction mixture is partitioned between CH$_2$Cl$_2$ and sat. NaHCO$_3$. The organic layer is dried (MgSO$_4$), filtered, and concentrated. The desired material is crystallized from CH$_2$Cl$_2$/MeOH/pentane to give 481 mg (67%) of the title compound as a crystalline solid. mp 163°–165° C.

Step 4

Preparation of N-hydroxy-2(R)-[(benzenesulfonyl)amino]-3-methyl butanamide

A suspension of N-benzyloxy-2(R)-[(benzenesulfonyl)amino]-3-methyl butanamide (100 mg, 0.280 mmol) and Pearlman's catalyst (25 mg) in MeOH (10 mL) is hydrogenated at 1 atmosphere for 3 hours. The mixture is filtered through celite, and the filtrate is concentrated. The desired material is crystallized from EtOAc/pentane to give 61 mg (80%) of the title compound as a crystalline solid. mp 154°–155° C.; IR (mineral oil) 3268, 2925, 2954, 2881, 2855, 1636, 1449, 1336, 1165, 694 cm$^{-1}$; $^1$H NMR (300 MHz, DMSO-d$_6$) δ10.53, 8.83, 7.98, 7.76, 7.50–7.65, 3.28, 1.65–1.85, 0.74, 0.70; MS (EI) m/z 272; Analysis: C, 48.37; H, 6.07; N, 10.14.

EXAMPLE 10

Preparation of N-Hydroxy-2-[(4-methoxybenzenesulfonyl)-amino]-3,3-dimethyl pentanamide

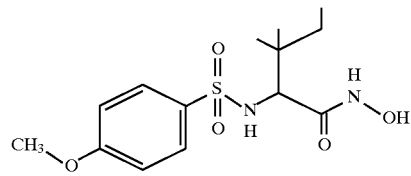

Step 1

Preparation of 2-[(4-methoxybenzenesulfonyl)amino]-3,3-dimethyl pentanoic acid 2-amino-3,3-dimethylpentanoic acid hydrochloride (1.63 g), (JCS Chem. Comm. 11, 830–1992) is mixed with diisopropylethylamine (3.6 g, 3.1 equivalent) in dry THF (100 mL). The 4-methoxybenzenesulfonyl chloride (1.86 g, 1 equivalent) is added as a solid. DMF (25 mL) is added to the resulting suspension. After stirring overnight at room temperature the solvents are removed under vacuum. The residue is partitioned between ethyl acetate (200 mL) and 1N HCl (100 mL). The organic phase is separated and the aqueous phase extracted with several more portions of ethyl acetate. The combined organic phases are washed with 1N HCl and then brine. The organic phase are dried (MgSO4), filtered, and concentrated under reduced pressure. The resulting crude product is loaded onto a reverse phase column as a DMSO solution. The column is eluted using a step gradient (10% increments), starting with 30% acetonitrile/water and ending at 90% acetonitrile/water. Combination of the appropriate fractions gave 116 mg of the title compound.

Step 2

Preparation of N-hydroxy-2-[(4-methoxybenzenesulfonyl)amino]-3,3-dimethyl pentanamide The product of step 1 (0.116 g), EDC hydrochloride (0.076 g, 1.1 equivalent), hydroxybenzotriazole (0.054 g, 1.1 equivalent), and diisopropylethylamine (0.143 g, 3 equivalent) are mixed with dichloromethane (20 mL) to give a homogeneous solution. Hydroxylamine hydrochloride (0.051 g, 2 equivalent) is added as a solid. DMF (3 mL) is added to solubilize the hydroxylamine hydrochloride. The reaction is allowed to stir at room temperature overnight. The solvents are then removed under reduced pressure and the residue partitioned between ethyl acetate and 1N HCl. The organic phase is separated and the aqueous phase re-extracted with ethyl acetate. The combined organic phases are dried (MgSO$_4$), filtered, and concentrated under reduced pressure. The crude product is loaded onto a reverse phase column as a DMSO solution. The column is eluted with a step gradient, starting at 20% acetonitrile/water, and raised in 10% increments. The appropriate fractions are combined to give 22 mg of the title compound. $^1$H NMR (DMSO, 300 MHz): 10.4, 7.69–7.65, 7.43, 7.01–6.98, 3.80, 1.20–1.17, 0.77, 0.75, 0.69 .

EXAMPLE 11

Biological Activity Test

Inhibitory activity is evaluated in one or more of the MMP enzymes (stromelysin, gelatinase, and collagenase) in vitro using particle concentration fluorescence assay. An inhibitor binds to MMP enzymes which prevents the degradation of a substrate by stromelysin, gelatinase, or collagenase. The substrate has attached to it a fluorescein and a biotin moiety. The intact substrate then binds to an avidin-coated particle via the biotin moiety. Once the particle is washed and dried, a fluorescent signal is generated since the fluorescent group is attached to the particle. Without an inhibitor present, the substrate is degraded by MMP enzymes and the fluorescein group is removed, therefore, no fluorescent signal can be detected. Testing compounds are dissolved in DMSO to the desired concentration, then the solutions are diluted to 1:5 with MMP buffer (50 mM Tris-HCl, pH 7.5; 150 mM NaCl; 0.02% $NaN_3$). Serial two-fold dilutions of each compound are prepared. A concentrated, activated enzyme solution is transferred into each plate of the testing compounds, and the mixture is incubated at room temperature for 15 minutes. Thawed MMP substrate is then added into all plates, and the plates are incubated in the dark for 1–3 hours at room temperature. At this point, the substrate mixture is mixed with 0.1% avidin-coated polystyrene particles. After 15 minutes, the fluorescence values are measured following filtration and washing of the beads. Ki values are then calculated. Inhibitory data for the compounds of this invention are shown in TABLE 1. Compounds with lower Ki values are expected to be more effective as MMP inhibitors. It is expected that a compound with a Ki less than 15 µM against stromelysin, collagenase, or gelatinase will display therapeutic effects in connective tissue disorders.

TABLE 1

MMP Inhibition Constants (Ki, uM) of the Compounds of the Invention

| Example No. | Gelatinase Ki (µM) | Example No. | Gelatinase Ki (µM) |
|---|---|---|---|
| 1 | 0.00781 | 2 | 0.0142 |
| 3 | 0.079 | 4 | 0.00723 |
| 5 | 0.0026 | 6 | 0.0121 |
| 7 | 0.0033 | 8 | 0.0091 |
| 9 | 0.082 | 10 | 0.0098 |

We claim:
1. A compound of formula I

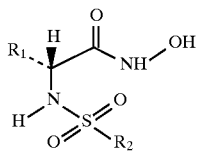

or pharmaceutical acceptable salts thereof wherein
$R_1$ is
 a) isopropyl,
 b) 2-methylbut-2yl
 c) phenyl,
 d) benzyl, or
 e) 1H-indol-3ylmethyl; and
$R_2$ is
 a) n-octyl,
 b) phenyl, or
 c) phenyl substituted with methoxy, fluoro, or bromo.

2. A compound of claim 1 wherein $R_2$ is selected from the group consisting of n-octyl, phenyl, p-methoxyphenyl, p-fluorophenyl, or p-bromophenyl.

3. A compound of claim 1 which is
 a. N-Hydroxy-2(R)-[(4-methoxybenzenesulfonyl)amino]-3-(3-indolyl)-propanamide,
 b. N-Hydroxy-2(R)-[(benzenesulfonyl)amino]-3-(3-indolyl)-propanamide,
 c. N-Hydroxy-2(R)-[(4-fluorobenzenesulfonyl)amino]-3-(3-indolyl)-propanamide,
 d. N-Hydroxy-2(R)-[(4-methoxybenzenesulfonyl)amino]-3-phenyl-propanamide,
 e. N-Hydroxy-2(R)-[(4-bromobenzenesulfonyl)amino]-3-(3-indolyl)-propanamide,
 f. N-Hydroxy-2(R)-[(n-octylsulfonyl)amino]-3-(3-indolyl)-propanamide,
 g. N-Hydroxy-2(R)-[(4-methoxybenzenesulfonyl)amino]-2-phenyl acetamide,
 h. N-Hydroxy-2(R)-[(4-methoxybenzenesulfonyl)amino]-3-methyl butanamide,
 i. N-Hydroxy-2(R)-[(benzenesulfonyl)amino]-3-methyl butanamide, or
 j. N-Hydroxy-2(R)-[(4-methoxybenzenesulfonyl)amino]-3,3-dimethyl pentanamide.

4. A method of inhibiting excess matrix metalloproteinase which comprises administering to a patient in need thereof an effective amount of a compound of claim 1.

5. A method of claim 4 wherein the matrix metalloproteinase is stromelysin, collagenase, and gelatinase.

6. A method of treating a disease involving connective tissue degradation which comprises administering to a patient in need thereof an effective amount of a compound of claim 1.

7. A method of claim 6 wherein the disease related to connective tissue degradation is osteoarthrits, rheumatoid arthritis, septic arthritis, osteopenias, osteoporosis, tumor metastasis, periodontitis, gingivitis, corneal ulceration, dermal ulceration, or gastric ulceration.

8. The method of claim 4 wherein the effective amount of the compound of claim 1 is administered orally, parenterally, or topically in a pharmaceutical composition.

9. The method of claim 6 wherein the effective amount of the compound of claim 1 is administered orally, parenterally, or topically in a pharmaceutical composition.

10. The method of claim 4 or 6 wherein said compound is administered in an amount of from about 0.1 to about 100 mg/kg of body weight/day.

11. A pharmaceutical composition which comprises an amount of the compound of claim 1 effective to inhibit excess matrix metalloproteinase and a pharmaceutically acceptable carrier.

* * * * *